United States Patent
Chang et al.

(10) Patent No.: US 10,603,448 B2
(45) Date of Patent: Mar. 31, 2020

(54) DISPOSABLE SYRINGE FOR PREVENTION OF REUSE

(71) Applicant: DAEIL RUBBER TECH CO., LTD., Incheon (KR)

(72) Inventors: Kyong Tae Chang, Anyang-si (KR); Man Soo Kim, Seoul (KR)

(73) Assignee: DAEIL RUBBER TECH CO., LTD., Incheon (KR)

( * ) Notice: Subject to any disclaimer, the term of this patent is extended or adjusted under 35 U.S.C. 154(b) by 160 days.

(21) Appl. No.: 15/575,349

(22) PCT Filed: Jun. 8, 2017

(86) PCT No.: PCT/KR2017/005948
§ 371 (c)(1),
(2) Date: Nov. 18, 2017

(87) PCT Pub. No.: WO2017/217692
PCT Pub. Date: Dec. 21, 2017

(65) Prior Publication Data
US 2018/0236183 A1 Aug. 23, 2018

(30) Foreign Application Priority Data
Jun. 13, 2016 (KR) .................. 10-2016-0072943

(51) Int. Cl.
*A61M 5/50* (2006.01)
*A61M 5/315* (2006.01)
*A61M 5/31* (2006.01)

(52) U.S. Cl.
CPC .......... *A61M 5/5013* (2013.01); *A61M 5/315* (2013.01); *A61M 5/31501* (2013.01); *A61M 5/31505* (2013.01); *A61M 5/50* (2013.01); *A61M 5/502* (2013.01); *A61M 5/3135* (2013.01); *A61M 2005/31508* (2013.01); *A61M 2005/5026* (2013.01); *A61M 2005/5033* (2013.01); *A61M 2205/273* (2013.01)

(58) Field of Classification Search
CPC ...... A61M 5/50; A61M 5/5013; A61M 5/502; A61M 5/31505; A61M 5/31501; A61M 5/315; A61M 5/3135; A61M 2005/5206; A61M 2005/5033; A61M 2005/31508; A61M 2205/273
See application file for complete search history.

(56) References Cited

U.S. PATENT DOCUMENTS

| | | | | |
|---|---|---|---|---|
| 5,304,138 A | * | 4/1994 | Mercado | A61M 5/50 604/110 |
| 6,494,863 B1 | * | 12/2002 | Shaw | A61M 5/3234 604/110 |

(Continued)

FOREIGN PATENT DOCUMENTS

KR 10-1660906 B1 9/2016

*Primary Examiner* — Nathan R Price
*Assistant Examiner* — Anh Bui
(74) *Attorney, Agent, or Firm* — KORUS Patent, LLC; Seong Il Jeong

(57) ABSTRACT

The present invention relates to a disposable syringe for the prevention of reuse, and more specifically to a disposable syringe for the prevention of reuse, which can restrain a plunger from moving after a medicine has been exhausted using the pressure of the plunger, thereby fundamentally preventing the syringe from being reused.

4 Claims, 6 Drawing Sheets

(56) References Cited

U.S. PATENT DOCUMENTS

| | | |
|---|---|---|
| 8,066,668 B2 | 11/2011 | Wayman et al. |
| 2010/0268160 A1 | 10/2010 | Eccard |
| 2014/0155826 A1* | 6/2014 | Yevmenenko ........ A61M 5/502 604/110 |

* cited by examiner

DISPOSABLE SYRINGE FOR PREVENTION OF REUSE

TECHNICAL FIELD

The present invention relates to a disposable syringe for the prevention of reuse, and more specifically to a disposable syringe for the prevention of reuse, which can restrain a plunger from moving after a medicine has been exhausted using the pressure of the plunger, thereby fundamentally preventing the syringe from being reused.

BACKGROUND ART

Among items for everyday life, there are many items which are prohibited from being reused after use by laws for the purpose of maintaining sanitation or social security. However, there are frequent cases where products prohibited from being reused are reused chiefly for an economic reason.

Therefore, it may be considered to be irresponsible to enact only a law prohibiting reuse and not to provide actual countermeasures against reuse. Accordingly, some items prohibited from being reused require that products themselves are disabled in connection with reuse by technical devices so that the products cannot be reused after use even when users desire to reuse them, in addition to the enactment of the law.

In particular, disposable syringes which must be discarded after use in principle in order to prevent infection have reusable structures. Accordingly, there are cases where disposable syringes are reused after being sterilized with hot water or the like. In the worst cases, syringes are reused without a sterilization process, and thus serious side effects are caused.

Since there are many cases where disposable syringes are reused a plurality of times in poor countries or by unscrupulous medical care providers, various diseases are widely infected through reused syringes, thereby causing social problems.

Recently, in order to overcome the above problem, many types of disposable syringes for the prevention of reuse have been developed.

However, the conventional disposable syringes for the prevention of reuse have the problem of low economic feasibility because they have complex structures and incur high manufacturing costs.

For example, in the case of some products, technical structures for the prevention of reuse are complex, and thus they have product prices which are 10 to 20 times the price of a general disposable syringe without a structure for the prevention of reuse, with the result that they are not actually used in front-line medical fields.

PRIOR ART DOCUMENT

Patent Document (Patent document 1) Korean Patent No. 10-1282209
(Patent document 2) Korean Utility Model Registration No. 20-0391370

DISCLOSURE

Technical Problem

The present invention has been conceived to overcome the above-described problems, and an object of the present invention is to provide a disposable syringe for the prevention of reuse, which can prevent a plunger from moving backward inside a cylinder after a medicine has been completely exhausted by the pressure of the plunger, thereby preventing the syringe from being reused.

Another object of the present invention is to provide a disposable syringe for the prevention of reuse, which can control the entry of a plunger into a cylinder through the fitting and separation of an entry prevention clip into and from the plunger, thereby preventing the plunger from being unintentionally introduced into the cylinder due to carelessness.

Technical Solution

In order to accomplish the above objects, the present invention provides a disposable syringe for the prevention of reuse, the disposable syringe including: a cylinder configured such that an injection needle is installed in one end portion thereof and an opening is formed in the other end portion thereof; a housing installed above the other end portion of the cylinder, and configured such that a through hole opposite to the opening of the cylinder is formed therein; a unidirectional entry portion formed in the through hole of the housing, and configured to form a conduit line extending from the through hole to the opening of the cylinder and to have elasticity so that the conduit line is spread; a plunger configured to generate pressure adapted to introduce a medicine into the cylinder or discharge a medicine from the inside of the cylinder through the injection needle, and to enter into the cylinder through the conduit line of the unidirectional entry portion; and confinement members formed along the circumference of the plunger, formed to have a larger diameter than the conduit line of the unidirectional entry portion, and configured to enter into the housing while spreading the conduit line of the unidirectional entry portion upon entry through the conduit line of the unidirectional entry portion.

In this case, the conduit line of the unidirectional entry portion is preferably formed by a plurality of split elastic segments.

Furthermore, a soft gasket is preferably coupled to one end of the plunger, and a push head formed to have a larger diameter than the plunger in order to enable the plunger to be gripped is preferably formed at the other end of the plunger; and the push head is preferably connected via a breakable neck which has a smaller diameter than the plunger.

Advantageous Effects

The disposable syringe for the prevention of reuse according to the present invention has the following effects:

First, when a medicine inside the cylinder is all discharged through the injection needle by the plunger, the confinement members formed on the plunger are stuck on ends of the elastic segments of the unidirectional entry portion, thereby restraining the plunger from moving backward.

As described above, once the medicine inside the cylinder has been all discharged through the forward movement of the plunger, the plunger is restrained from moving backward because the confinement members are struck on ends of the elastic segments, thereby fundamentally restraining a medicine from being introduced into the cylinder and thus preventing the disposable syringe from being reused.

Second, the entry prevention clip is provided to be selectively fitted into and separated from the plunger, thereby preventing the plunger from entering into the cylinder in the state in which the use of the syringe is not desired.

In other words, the plunger can be restrained from entering into the cylinder by using the entry prevention clip which is selectively fitted into and separated from the plunger.

As a result, the present invention has an effect of preventing the syringe from being wasted because the reuse of the syringe is made impossible due to the entry of the plunger which is performed before a medicine is introduced into the cylinder.

MODE FOR INVENTION

Figure 1:
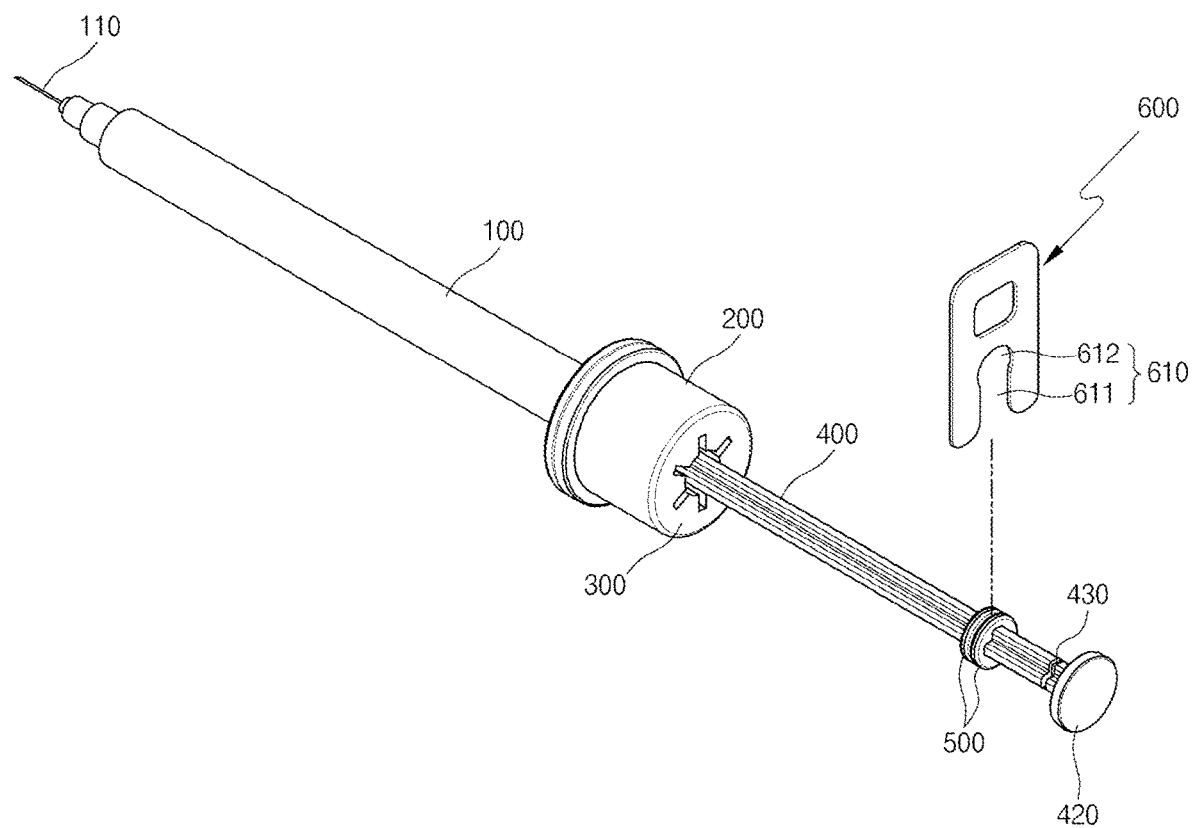
FIG. 1 is a perspective view showing a disposable syringe for the prevention of reuse according to a preferred embodiment of the present invention.

The terms or words used in the present specification and the claims should not be interpreted as being limited to common or dictionary meanings, but should be interpreted as having meanings and concepts suitable for the technical spirit of the invention based on the principle in which an inventor may appropriately define the concepts of terms in order to describe his or her invention in the best way.

A disposable syringe for the prevention of reuse according to a preferred embodiment of the present invention will be described with reference to the accompanying FIGS. 1 to 6.

The disposable syringe for the prevention of reuse has a technical feature in which a separate housing configured such that a unidirectional entry portion is installed therein is provided on a cylinder and a plunger configured to be prevented from moving backward by being struck on the unidirectional entry portion is provided.

Accordingly, once a medicine accommodated inside the cylinder has been all exhausted through the movement of the plunger, the plunger cannot be removed from the cylinder, thereby preventing the syringe from being reused.

The disposable syringe for the prevention of reuse is configured to include a cylinder 100, a housing 200, a unidirectional entry portion 300, a plunger 400, confinement members 500, and an entry prevention clip 600.

The cylinder 100 provides a space in which a medicine is accommodated. An injection needle 110 through which the medicine is introduced and discharged is coupled into one end portion of the cylinder 100, and an opening 120 through which the plunger 400 enters into and exits from the inside of the cylinder is formed in the other end portion of the cylinder 100.

Next, the housing 200 is provided with the unidirectional entry portion 300 configured to prevent the plunger 400 from being removed from the cylinder 100 after the medicine has been all exhausted inside the cylinder 100. A predetermined internal space in which the unidirectional entry portion 300 is installed is formed in the housing 200.

The housing 200 is installed above the opening 120 formed in the other end portion of the cylinder 100, and a through hole 210 corresponding to the opening is formed in the housing 200.

Next, the unidirectional entry portion 300 functions to prevent the plunger 400 from being removed from the cylinder 100 when the medicine has been all exhausted inside the cylinder 100, and is formed in the through hole 210 of the housing 200.

The unidirectional entry portion 300 forms a conduit line, through which the plunger 400 passes, between the housing 200 and the opening 120 of the cylinder 100.

The diameter of the conduit line is formed to be smaller than that of the confinement members 500 to be described later.

In this case, although not limited to this, the conduit line may be formed to decrease gradually from the through hole 210 of the housing 200 to the opening 120.

This is intended to enable the confinement members 500 to be effectively struck on an end of the unidirectional entry portion 300 when the confinement members 500 are located inside the housing 200.

Meanwhile, the material of the unidirectional entry portion 300 is preferably an elastic material.

This is intended to enable the confinement members 500, passing through the conduit line of the unidirectional entry portion 300, to spread the unidirectional entry portion 300 outward in order to extend the conduit line.

Figure 2:
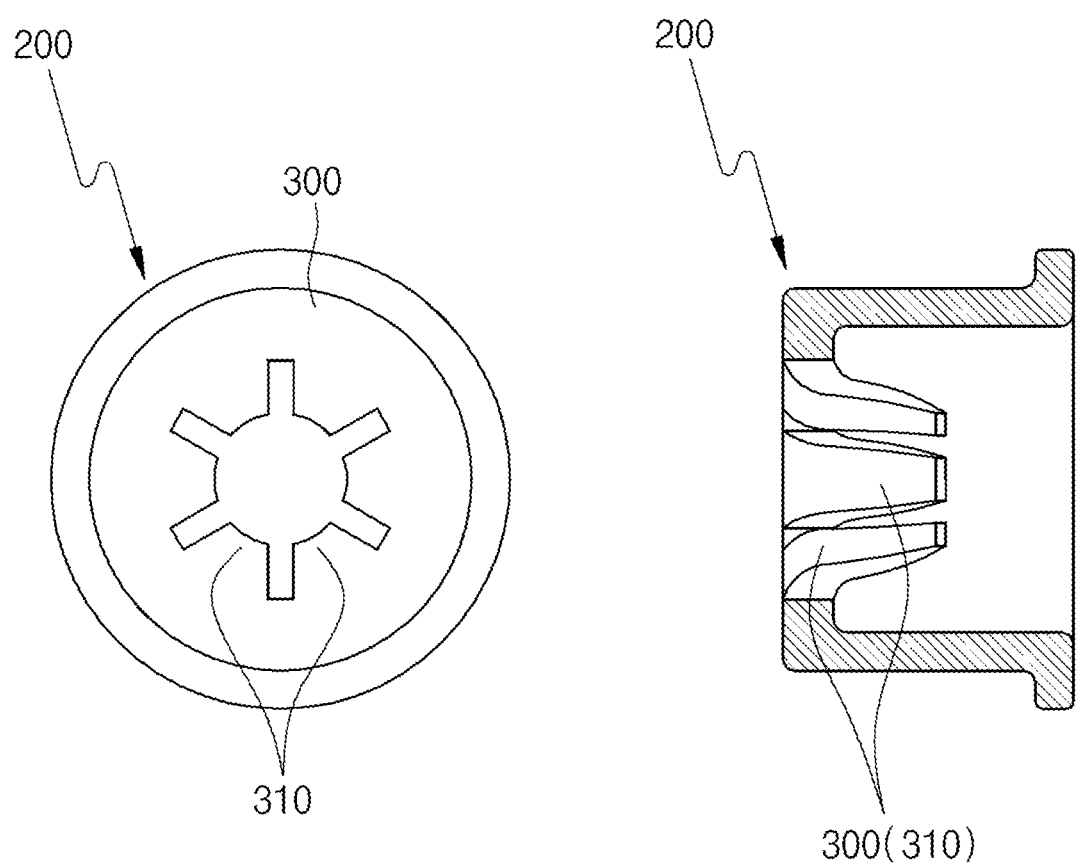
FIG. 2 is a view showing the housing and unidirectional entry portion of the disposable syringe for the prevention of reuse according to the preferred embodiment of the present invention.

In this case, the unidirectional entry portion 300 is preferably provided as split elastic segments 310, as shown in FIG. 2.

The conduit line of the unidirectional entry portion 300 is formed by the plurality of elastic segments 310 as described above, and thus the extension of the conduit line can be further easily performed.

Next, the plunger 400 functions to control pressure inside the cylinder 100, and to introduce a medicine into the cylinder 100 or discharge a medicine from the cylinder 100 to the outside.

In other words, the plunger 400 controls the entry and exit of a medicine while generating a positive or negative pressure inside the cylinder 100.

The length of the plunger 400 preferably corresponds to that of the cylinder 100. A gasket 410 and a push head 420 are installed at one and other ends of the plunger 400, respectively.

The gasket 410 prevents a medicine from leaking through the plunger 400 by maintaining the water-tightness in connection with the inner circumferential surface of the cylinder 100.

The push head 420 functions to facilitate a grip on the plunger 400. The diameter of the push head 420 is formed to be larger than that of the plunger 400.

In this case, the push head 420 is formed at an end of the plunger 400, and is connected via a breakable neck 430 which has a smaller diameter than the plunger 400.

In other words, the breakable neck 430 connects the plunger 400 and the push head 420 to each other, and is formed to have a smaller diameter. Accordingly, when a user forcibly pulls the plunger 400 while holding the push head 420 in order to reuse the syringe in the state shown in FIG. 6, the breakable neck 430 is cut off, thereby fundamentally preventing the syringe from being reused.

Next, the confinement members 500 function to confine the plunger 400 in the cylinder 100 in order to prevent the plunger 400 from moving backward after the plunger 400 has been inserted into the cylinder 100 in order to discharge a medicine inside the cylinder 100, and is formed along the circumference of the plunger 400.

The confinement members 500 are preferably formed in circular shapes, and are formed to have a larger diameter than the plunger 400.

Furthermore, the confinement members 500 are formed to have a larger diameter than the conduit line of the unidirectional entry portion 300, and need to be formed to have a diameter which enables the confinement members 500 to enter into the housing 200 while spreading the elastic segments 310 which form the unidirectional entry portion 300.

The reason for this is that when the diameter of the confinement members 500 is excessively large, the passage of the plunger 400 through the unidirectional entry portion 300 is obstructed, and thus the use of the syringe is also obstructed.

In other words, the confinement members 500 are configured to be stuck at ends of the elastic segments 310 forming the unidirectional entry portion 300 after passing through the conduit line of the unidirectional entry portion 300, thereby restraining the plunger 400 from moving backward.

Figure 3:
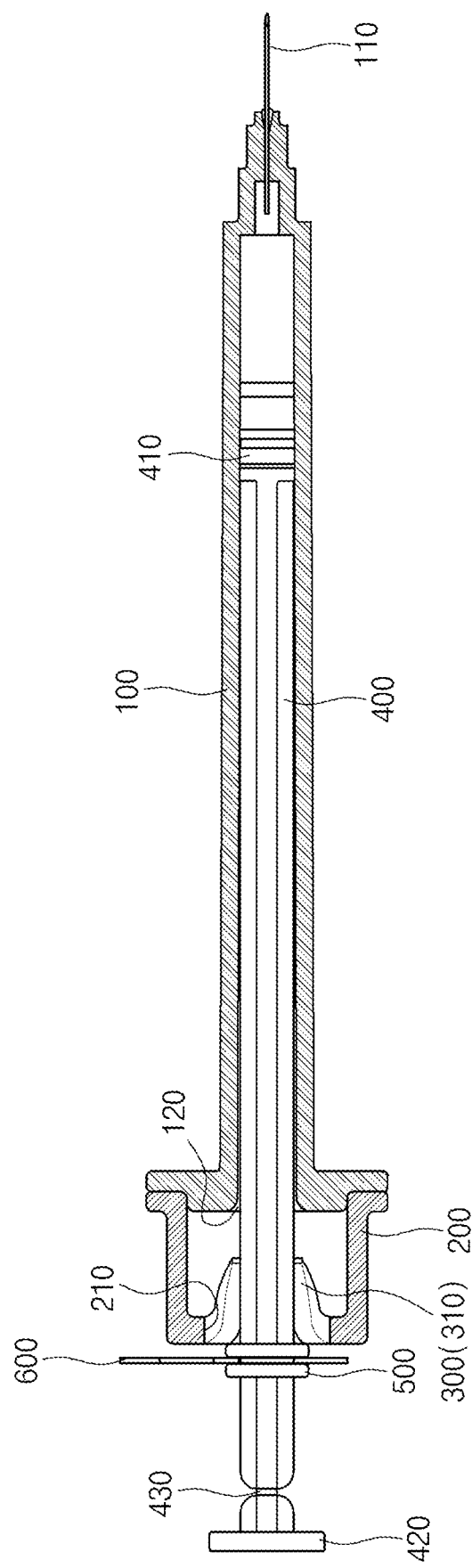
FIG. 3 is a side sectional view showing a state before the use of the disposable syringe for the prevention of reuse according to the preferred embodiment of the present invention.
Figure 4:
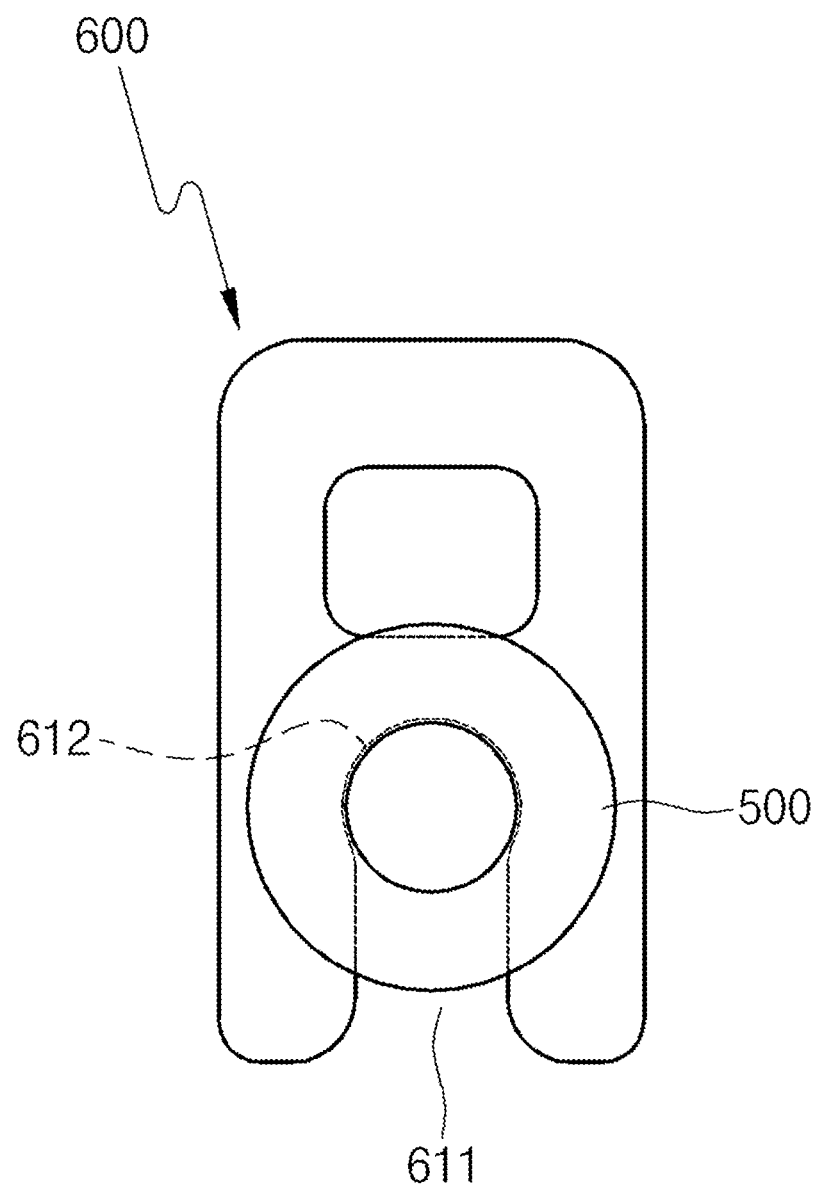
FIG. 4 is a view showing a state in which an entry prevention clip has been fitted before the use of the disposable syringe for the prevention of reuse according to the preferred embodiment of the present invention.

In this case, the confinement members 500 are preferably a pair of confinement members in the lengthwise direction of the plunger 400, as shown in FIGS. 1 and 3.

When the confinement members 500 are a pair of confinement members as described above, a space (gap) is formed between the pair of confinement members 500.

The space is a configuration into which the entry prevention clip 600 to be described later is fitted.

Next, the entry prevention clip 600 functions to restrain the plunger 400 from entering into the cylinder 100 in normal times.

The technical feature of the syringe according to the present invention cylinder 100 lies in that the reuse of the syringe is prevented by preventing the entered plunger 400 from being removed from the cylinder 100. In this case, if the plunger 400 enters into the cylinder unintentionally before the syringe is used, the syringe cannot be used and thus wasted. In order to prevent this problem, the entry prevention clip 600 is provided.

The entry prevention clip 600 is formed to be fitted into the confinement members 500. A coupling recess 610 whose one side is open is formed in the entry prevention clip 600.

The coupling recess 610 includes an entry portion 611 and an engagement portion 612.

The entry portion 611 functions to guide the part of the plunger 400, disposed between the pair of confinement members 500, to the engagement portion 612, and the width of the entry portion 611 is formed to be smaller than the diameter of the plunger 400.

The engagement portion 612 is a portion which is stuck on the circumference of the plunger 400, and is formed in a shape corresponding to the external diameter of the plunger 400.

The engagement portion 612 is formed in a circular shape, and the diameter of the engagement portion 612 corresponds to that of the plunger 400.

Using the configuration of the coupling recess 610, when the entry prevention clip 600 is fitted into the plunger 400, the entry portion 611 of the entry prevention clip 600 is spread outward by the plunger 400 and inserted over the outer circumferential surface of the plunger 400 in the engagement portion 612, thereby enabling the entry prevention clip 600 to be fitted into the plunger 400.

The operation of the disposable syringe for the prevention of reuse configured as described above will be described below.

FIG. 3 shows a syringe in an initial state, in which state the most part of the plunger 400 has been introduced into the cylinder 100, and the entry prevention clip 600 has been fitted between the pair of confinement members 500, thereby restraining the overall plunger 400 from entering into the cylinder 100.

In the state, when a user desires to use the syringe, the entry prevention clip 600 is separated from the confinement members 500.

In this case, when the entry prevention clip 600 is pulled, the entry portion 611 of the coupling recess 610 interferes with the plunger 400, and is then spread to both sides thereof, thereby enabling the entry prevention clip 600 to be separated from the plunger 400.

As the entry prevention clip 600 is separated from the plunger 400, the movement of the plunger 400 is made free.

Figure 5:
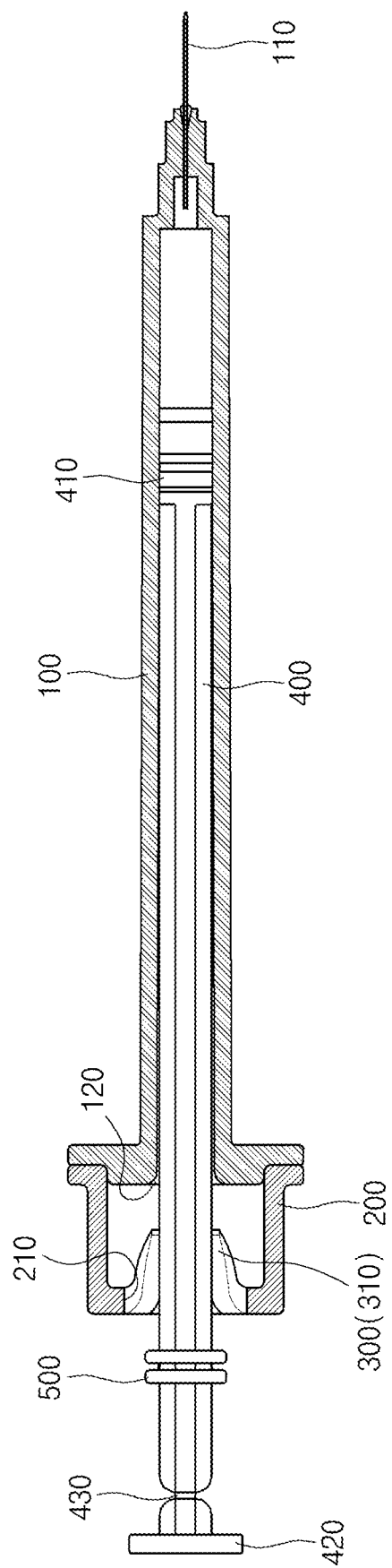
FIG. 5 is a side sectional view showing a state in which a plunger has been moved backward to inject a medicine after the separation of the entry prevention clip in order to use the disposable syringe for the prevention of reuse according to the preferred embodiment of the present invention.

Next, the user introduces a medicine by generating a negative pressure inside the cylinder 100 through the pulling of the plunger 400, as shown in FIG. 5.

Next, when pressing is performed by pushing the push head 420 of the plunger 400 in the state in which the injection needle 110 has been inserted into the skin of a patient, a positive pressure is generated inside the cylinder 100, and thus the medicine is discharged through the injection needle 110.

Figure 6:
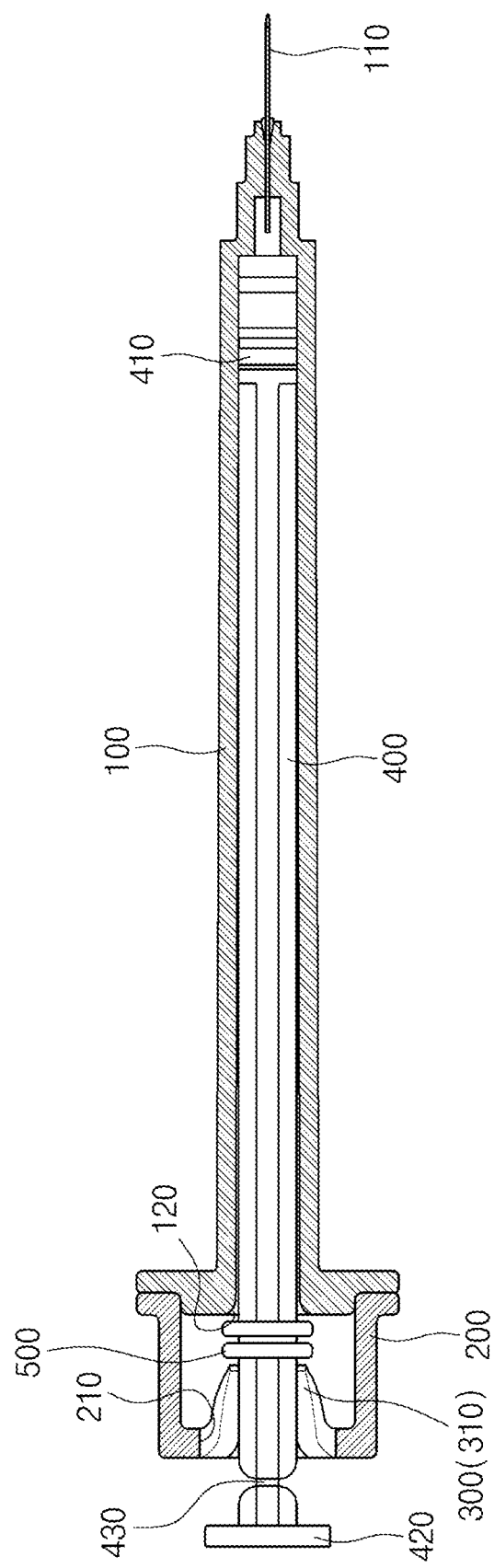
FIG. 6 is a side sectional view showing a state in which the use of the disposable syringe for the prevention of reuse according to the preferred embodiment of the present invention has been completed.

In this case, the confinement members 500 formed along the circumference of the plunger 400 ensure a conduit line while spreading the elastic segments 310 of the unidirectional entry portion 300, and are introduced into the housing 200, as shown in FIG. 6.

Thereafter, when the confinement members 500 are located inside the housing 200, the plurality of elastic segments 310 is returned to their original positions by their restoring force, and the confinement members 500 come into contact with ends of the elastic segments 310.

Accordingly, even when the plunger 400 is pulled, the confinement members 500 are stuck on the ends of the elastic segments 310 of the unidirectional entry portion 300, as shown in FIG. 6, thereby enabling the plunger 400 from being separated from the cylinder 100.

According to the above-described principle, the reuse of the syringe can be fundamentally prevented.

As described above, the disposable syringe for the prevention of reuse according to the present invention has a technical feature in which the housing 200 configured such that the unidirectional entry portion 300 is formed therein is installed above the opening 120 of the cylinder 100 and the confinement members 500 configured to move forward while spreading one side of the unidirectional entry portion 300 and be then struck on the other side of the unidirectional entry portion 300, thereby restraining the plunger 400 from being returned to its original position, are formed on the plunger 400.

As a result, the reuse of the disposable syringe can be fundamentally prevented, thereby preventing infection attributable to the reuse of the syringe.

Although the present invention has been described with reference to the described specific embodiments in detail below, it will be apparent to a person skilled in the art that various modifications and alterations may be made within the scope of the technical spirit of the present invention, and it will be also apparent that such modifications and alterations fall within the attached claims.

DESCRIPTION OF REFERENCE SYMBOLS

100: cylinder
110: injection needle
120: opening
200: housing
210: through hole
300: unidirectional entry portion
310: elastic segments
400: plunger
410: gasket
420: push head
430: breakable neck
500: confinement members
600: entry prevention clip
610: coupling recess
611: entry portion
612: engagement portion

The invention claimed is:

1. A disposable syringe for prevention of reuse, the disposable syringe comprising:
a cylinder configured such that an injection needle is installed in one end portion thereof and an opening is formed in a remaining end portion thereof;
a housing installed above the remaining end portion of the cylinder, and configured such that a through hole opposite to the opening of the cylinder is formed therein;
a unidirectional entry portion formed in the through hole of the housing, and configured to form a conduit line extending from the through hole to the opening of the cylinder and to have elasticity so that the conduit line is spreadable;
a plunger configured to generate pressure adapted to introduce a medicine into the cylinder or discharge a medicine from an inside of the cylinder through the injection needle, and to enter into the cylinder through the conduit line of the unidirectional entry portion; and
confinement members formed along a circumference of the plunger, formed to have a larger diameter than the conduit line of the unidirectional entry portion, and configured to enter into the housing while spreading the conduit line of the unidirectional entry portion upon entry through the conduit line of the unidirectional entry portion, the confinement members being disposed at a predetermined position of one end portion of the plunger such that, when the medicine is fully discharged from the inside of the cylinder by the plunger, the confinement members are located between the unidirectional entry portion and the opening of the cylinder.

2. The disposable syringe of claim 1, wherein the conduit line of the unidirectional entry portion is formed by a plurality of split elastic segments.

3. The disposable syringe of claim 1, wherein:
a soft gasket is coupled to one end of the plunger, and a push head formed to have a larger diameter than the plunger in order to enable the plunger to be gripped is formed at a remaining end of the plunger; and
the push head is connected via a breakable neck which has a smaller diameter than the plunger.

4. The disposable syringe of claim 1, wherein:
an entry prevention clip configured to be selectively fitted into and separated from the plunger is provided on the part of the plunger between the confinement members and the injection needle; and
the entry prevention clip is formed to be larger than the through hole of the housing to thus prevent the confinement members from entering into the housing.

* * * * *